US008398628B2

(12) United States Patent
Muller (10) Patent No.: US 8,398,628 B2
(45) Date of Patent: Mar. 19, 2013

(54) EYE THERAPY SYSTEM (75) Inventor: David Muller, Boston, MA (US)

(73) Assignee: Avedro, Inc., Waltham, MA (US)

( * ) Notice: Subject to any disclaimer, the term of this patent is extended or adjusted under 35 U.S.C. 154(b) by 727 days.

(21) Appl. No.: 12/562,625

(22) Filed: Sep. 18, 2009

(65) Prior Publication Data
US 2010/0076423 A1 Mar. 25, 2010

Related U.S. Application Data (60) Provisional application No. 61/098,489, filed on Sep. 19, 2008, provisional application No. 61/101,503, filed on Sep. 30, 2008.

(51) Int. Cl.
A61B 18/12 (2006.01)
(52) U.S. Cl. .......................................... 606/41
(58) Field of Classification Search .................. 606/27, 606/34, 41
See application file for complete search history.

(56) References Cited

U.S. PATENT DOCUMENTS

| 3,776,230 | A | | 12/1973 | Neefe |
|---|---|---|---|---|
| 4,326,529 | A | | 4/1982 | Doss et al. |
| 4,381,007 | A | | 4/1983 | Doss |
| 4,481,948 | A | * | 11/1984 | Sole ........................... 606/45 |
| 4,490,022 | A | | 12/1984 | Reynolds |
| 4,712,543 | A | | 12/1987 | Baron |
| 4,743,725 | A | | 5/1988 | Risman |
| 4,796,623 | A | | 1/1989 | Krasner et al. |
| 4,805,616 | A | | 2/1989 | Pao |
| 4,881,543 | A | | 11/1989 | Trembly et al. |
| 4,891,043 | A | | 1/1990 | Zeimer et al. |
| 4,994,058 | A | | 2/1991 | Raven et al. |
| 5,103,005 | A | | 4/1992 | Gyure et al. |
| 5,171,254 | A | | 12/1992 | Sher |
| 5,281,211 | A | | 1/1994 | Parel et al. |
| 5,332,802 | A | | 7/1994 | Kelman et al. |
| 5,370,644 | A | | 12/1994 | Langberg |
| 5,437,658 | A | | 8/1995 | Muller et al. |

(Continued)

FOREIGN PATENT DOCUMENTS

| EP | 1 561 440 | 8/2005 |
|---|---|---|
| EP | 1 790 383 | 5/2007 |

(Continued)

OTHER PUBLICATIONS

Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.

(Continued)

Primary Examiner — Michael Peffley
Assistant Examiner — Daniel Fowler
(74) Attorney, Agent, or Firm — Nixon Peabody LLP (57) ABSTRACT The cornea is reshaped in multiple steps according to varying amounts of energy in varying patterns and/or at varying locations to achieve a customized reshaping of the cornea to address the specific needs of an individual patient. The varying amounts of energy may be applied via one or more conducting elements, which include an outer conductor and an inner conductor disposed within the outer conductor, a distal end of the outer conductor and the inner conductor defining the varying patterns. For example, one step may form a substantially circular lesion to flatten a first portion of the cornea to treat presbyopia, while another step may form a substantially circular and concentric lesion having a greater diameter to steepen a second portion of the cornea to treat hyperopia. Advantageously, continuous transitional regions are formed relative to the reshaped portions to provide vision for intermediate distances.

11 Claims, 9 Drawing Sheets

U.S. PATENT DOCUMENTS

| | | | |
|---|---|---|---|
| 5,461,212 A | 10/1995 | Seiler et al. | |
| 5,490,849 A | 2/1996 | Smith | |
| 5,586,134 A | 12/1996 | Das et al. | |
| 5,618,284 A | 4/1997 | Sand | |
| 5,624,456 A | 4/1997 | Hellenkamp | |
| 5,634,921 A | 6/1997 | Hood et al. | |
| 5,658,278 A | 8/1997 | Imran et al. | |
| 5,766,171 A | 6/1998 | Silvestrini | |
| 5,779,696 A | 7/1998 | Berry et al. | |
| 5,814,040 A | 9/1998 | Nelson et al. | |
| 5,830,139 A | 11/1998 | Abreu | |
| 5,873,901 A | 2/1999 | Wu et al. | |
| 5,885,275 A | 3/1999 | Muller | |
| 5,910,110 A | 6/1999 | Bastable | |
| 5,919,222 A | 7/1999 | Hjelle et al. | |
| 6,033,396 A | 3/2000 | Huang et al. | |
| 6,036,688 A * | 3/2000 | Edwards | 606/34 |
| 6,053,909 A | 4/2000 | Shadduck | |
| 6,104,959 A | 8/2000 | Spertell | |
| 6,139,876 A | 10/2000 | Kolta | |
| 6,149,646 A | 11/2000 | West, Jr. et al. | |
| 6,161,544 A | 12/2000 | DeVore et al. | |
| 6,162,210 A | 12/2000 | Shadduck | |
| 6,213,997 B1 * | 4/2001 | Hood et al. | 606/5 |
| 6,293,938 B1 | 9/2001 | Muller | |
| 6,319,273 B1 | 11/2001 | Chen et al. | |
| 6,325,792 B1 | 12/2001 | Swinger et al. | |
| 6,334,074 B1 | 12/2001 | Spertell | |
| 6,342,053 B1 | 1/2002 | Berry | |
| 6,402,739 B1 | 6/2002 | Neev | |
| 6,413,255 B1 | 7/2002 | Stern | |
| 6,520,956 B1 | 2/2003 | Huang | |
| 6,617,963 B1 | 9/2003 | Watters et al. | |
| 6,749,604 B1 | 6/2004 | Eggers et al. | |
| 6,946,440 B1 | 9/2005 | DeWoolfson | |
| 7,044,945 B2 | 5/2006 | Sand | |
| 7,130,835 B2 | 10/2006 | Cox et al. | |
| 7,141,049 B2 | 11/2006 | Stern et al. | |
| 7,192,429 B2 | 3/2007 | Trembly | |
| 7,270,658 B2 | 9/2007 | Woloszko et al. | |
| 7,402,562 B2 | 7/2008 | DeWoolfson | |
| 7,713,268 B2 | 5/2010 | Trembly | |
| 2002/0002369 A1 | 1/2002 | Hood | |
| 2002/0013579 A1 | 1/2002 | Silvestrini | |
| 2002/0049437 A1 | 4/2002 | Silvestrini | |
| 2002/0077699 A1 | 6/2002 | Olivieri et al. | |
| 2002/0099363 A1 | 7/2002 | Woodward et al. | |
| 2002/0164379 A1 | 11/2002 | Nishihara et al. | |
| 2003/0018255 A1 | 1/2003 | Martin et al. | |
| 2003/0097130 A1 | 5/2003 | Muller et al. | |
| 2003/0175259 A1 | 9/2003 | Karageozian | |
| 2003/0216728 A1 | 11/2003 | Stern et al. | |
| 2004/0001821 A1 | 1/2004 | Silver et al. | |
| 2004/0111086 A1 | 6/2004 | Trembly | |
| 2004/0143250 A1 | 7/2004 | Trembly | |
| 2004/0199158 A1 | 10/2004 | Hood et al. | |
| 2004/0243160 A1 | 12/2004 | Shiuey et al. | |
| 2005/0033202 A1 | 2/2005 | Chow et al. | |
| 2005/0070977 A1 | 3/2005 | Molina | |
| 2005/0197657 A1 | 9/2005 | Goth et al. | |
| 2005/0241653 A1 * | 11/2005 | Van Heugten et al. | 128/898 |
| 2005/0287217 A1 | 12/2005 | Levin et al. | |
| 2006/0135957 A1 | 6/2006 | Panescu | |
| 2006/0149343 A1 | 7/2006 | Altshuler et al. | |
| 2006/0189964 A1 | 8/2006 | Anderson et al. | |
| 2006/0206110 A1 | 9/2006 | Knowlton et al. | |
| 2006/0254851 A1 | 11/2006 | Karamuk | |
| 2006/0287662 A1 | 12/2006 | Berry et al. | |
| 2007/0048340 A1 | 3/2007 | Ferren et al. | |
| 2007/0055227 A1 | 3/2007 | Khalaj et al. | |
| 2007/0074722 A1 | 4/2007 | Giroux et al. | |
| 2007/0114946 A1 | 5/2007 | Goetze et al. | |
| 2007/0123845 A1 | 5/2007 | Lubatschowski | |
| 2007/0161976 A1 | 7/2007 | Trembly | |
| 2007/0179564 A1 | 8/2007 | Harold | |
| 2007/0203547 A1 | 8/2007 | Costello et al. | |
| 2007/0244470 A1 | 10/2007 | Barker et al. | |
| 2007/0244496 A1 | 10/2007 | Hellenkamp | |
| 2008/0015660 A1 | 1/2008 | Herekar | |
| 2008/0027328 A1 | 1/2008 | Klopotek et al. | |
| 2009/0024117 A1 | 1/2009 | Muller | |
| 2009/0054879 A1 | 2/2009 | Berry | |
| 2009/0069798 A1 | 3/2009 | Muller et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187173 A1 | 7/2009 | Muller | |
| 2009/0209954 A1 | 8/2009 | Muller et al. | |
| 2010/0094197 A1 | 4/2010 | Marshall et al. | |

FOREIGN PATENT DOCUMENTS

| | | |
|---|---|---|
| EP | 2 269 531 | 1/2011 |
| WO | WO 99/17690 | 4/1999 |
| WO | WO 00/09027 | 2/2000 |
| WO | 0074648 A2 | 12/2000 |
| WO | WO 2004/052223 | 6/2004 |
| WO | 2006128038 A2 | 11/2006 |
| WO | WO 2006/128038 A2 | 11/2006 |
| WO | WO 2007/022993 | 3/2007 |
| WO | 2007/120457 A2 | 10/2007 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Berjano et. al.; "Ring Electrode for Radio-Frequency Heating of the Cornea: Modelling and In Vitro Experiments"; Medical & Biological Engineering & Computing 2003; vol. 41; pp. 630-639.
International Search Report mailed Aug. 14, 2009 for PCT/US2009/042204, (5 pages).
International Search Report mailed Nov. 20, 2009 for PCT/2009/059061 (3 pages).
International Search Report mailed Nov. 6, 2009 for PCT/US2009/057481 (2 pages).
European Search Report and Written Opinion for corresponding application EP 09 815 266.3, dated Feb. 7, 2012 (7 pages).
Chandonnet, CO2 Laser Annular Thermokeratoplasty: A Preliminary Study, Lasers in Surgery and Medicine 12:264-273 (1992), Wiley-Lill, Inc.
Muller et al., Br. J. Opthalmol 2001; 85:437-443 (April).
Naoumidi et al., J. Cataract Refract Surg. May 2006; 32(5):732-41.
Pallikaris et al., J. Cataract Refract Surg. Aug. 2005; 31(8):1520-29.
Acosta et al., Cornea. Aug. 2006;25(7):830-8.
International Search Report for PCT/US2010/029806 dated Jun. 1, 2010 (3 pages).
Written Opinion for PCT/US2010/029806 dated Jun. 1, 2010 (6 pages).
International Search Report for PCT/US2010/029791 dated Jun. 1, 2010 (3 pages).
Written Opinion for PCT/US2010/029791 dated Jun. 1, 2010 (6 pages).
Trembly et al.; Microwave Thermal Keratoplasty for Myopia: Keratoscopic Evaluation in Procine Eyes; Journal of Refractive Surgery; vol. 17; Nov./Dec. 2001; (8 pages).
Written Opinion corresponding to International Patent Application U.S. Appl. No. PCT/ US2009/057481, United States Patent Office; dated Nov. 6, 2009 (8 pages).
Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).
Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).
Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).
Andreassen TT, Simonsen AH, Oxlund H, "Biomechanical Properties of Keratoconus and Normal Corneas," *Experimental Eye Research*, vol. 31, Oct. 1980, pp. 435-441 (7 pages).

Anschutz T, "Laser Correction of Hyperopia and Presbyopia," *International Ophthalmology Clinics*, vol. 34, No. 4, Fall 1994, pp. 107-137 (33 pages).
Bailey MD, Zadnik K, "Outcomes of LASIK for Myopia With FDA-Approved Lasers," *Cornea*, vol. 26, No. 3, Apr. 2007, pp. 246-254 (9 pages).
Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).
Bower KS, Weichel ED, Kim TJ, "Overview of Refractive Surgery," *Am Fam Physician*, vol. 64, No. 7, Oct. 2001, pp. 1183-1190 (8 pages).
Braun EH, Lee J, Steinert RF, "Monovision in LASIK," *Ophthalmology*, vol. 115, No. 7, Jul. 2008, pp. 1196-1202 (7 pages).
Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).
Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).
Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).
Charman WN, "The Eye in Focus: Accommodation and Presbyopia," *Clinical and Experimental Optometry*, vol. 91, May 2008, pp. 207-225 (19 pages).
Corbett et al, "Effect of Collagenase Inhibitors on Coreal Haze after PRK", Exp. Eye Res., vol. 72, Issue 3, pp. 253-259, dated Jan. 29, 2001 (7 pages).
Cox CA, Krueger RR, "Monovision with Laser Vision Correction," *Ophthalmology Clinics of North Amermica*, vol. 19, No. 1, Mar. 2006, pp. 71-75 (7 pages).
Doss JD, Albillar JI, "A Technique for the Selective Heating of Corneal Stroma," *Contact & Intraocular Lens Medical Journal*, vol. 6, No. 1, Jan.-Mar. 1980, pp. 13-17 (8 pages).
Elsheikh A, Anderson K, "Comparative Study of Corneal Strip Extensometry and Inflation Tests," *Journal of the Royal Society Interface*, vol. 2, May 2005, pp. 177-185 (10 pages).
Evans BJW, "Monovision: a Review," *Ophthalmic and Physiological Optics*, vol. 27, Jan. 2007, pp. 417-439 (23 pages).
Gasset AA, Kaufman HE, "Thermokeratoplasty in the Treatment of Keratoconus," *American Journal of Ophthalmology*, vol. 79, Feb. 1975, pp. 226-232 (8 pages).
Gloster J, Perkins ES, "The Validity of the Imbert-Flick Law as Applied to Applanation Tonometry," *Experimental Eye Research*, vol. 2, Jul. 1963, pp. 274-283 (10 pages).
Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).
Hamilton DR, Hardten DR, Lindstrom RL, "Thermal Keratoplasty," *Cornea*, 2$^{nd}$ Edition, Chapter 167, 2005, pp. 2033-2045 (13 pages).
Hersh PS, "Optics of Conductive Keratoplasty: Implication for Presbyopia Management," *Transactions of the American Ophthalmological Society*, vol. 103, 2005, pp. 412-456 (45 pages).
Hjortdal JO, "Extensibility of the Normo-Hydrated Human Cornea," *Acta Ophthalmologica Scandinavica*, vol. 73, No. 1, Feb. 1995, pp. 12-17 (7 pages).
Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).
Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).
Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).
Jin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).

Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).
Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).
Loarie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).
Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).
McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).
McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).
Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).
Nash IS, Greene PR, Foster CS, "Comparison of Mechanical Properties of Keratoconus and Normal Corneas," *Experimental Eye Research*, vol. 35, 1982, pp. 413-424 (12 pages).
Newman JM, "Analysis, Interpretation, and Prescription for the Ametropias and Heterophorias," *Borish's Clinical Refraction*, 1998, pp. 776-822 (49 pages).
Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).
Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).
Petroll WM, Roy P, Chuong CT, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).
Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).
Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).
Pinsky PM, Datye DV, "Numerical Modeling of Radial, Astigmatic, and Hexagonal Keratotomy," *Refractive and Corneal Surgery*, vol. 8, No. 2, Mar.-Apr. 1992, pp. 164-172 (11 pages).
Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).
Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).
Rosenbloom A, "New Aged and Old Aged: Impact of the Baby Boomer," *Journal of the American Optometry Association*, vol. 74, No. 4, Apr. 2003, pp. 211-213 (5 pages).
Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).

Seiler T, Matallana M, Bende T, "Laser Thermokeratoplasty by Means of a Pulsed Holmium:YAG Laser for Hyperopic Correction," *Refractive and Corneal Surgery*, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" *Refractive and Corneal Surgery*, vol. 8, No. 2, Mar.-Apr. 1992, pp. 139-142 (6 pages).

Shin TJ, Vito RP, Johnson LW, McCarey BE, "The Distribution of Strain in the Human Cornea," *Journal of Biomechanics*, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL., "LASIK World Literature Review: Quality of Life and Patient Satisfaction," *Ophthalmology*, vol. 116, No. 4, Apr. 2009, pp. 691-701 (11 pages).

Stanley PF, Tanzer DJ, Schallhorn SC, "Laser Refractive Surgery in the United States Navy," *Current Opinion Ophthalmology*, vol. 19, Jul. 2008, pp. 321-324 (4 pages).

Strenk SA, Strenk LM, Koretz JF, "The Mechanism of Presbyopia," *Progress in Retinal Eye Research*, vol. 24, May 2005, pp. 379-393 (15 pages).

Stringer H, Parr J., "Shrinkage Temperature of Eye Collagen," *Nature*, Dec. 1964, p. 1307 (1 page).

Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).

Telandro A., "Pseudo-Accommodation Cornea: A New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).

Wollensak, G., et al., "Riboflavin/Ultraviolet-A—Induced Collagen Crosslinking for the Treatment of Keratoconus," *American Journal of Ophthalmology, Ophthalmic Publ.*, Chicago, IL, US, vol. 135, No. 5, May 1, 2003, pp. 620-627 (8 pages).

Zelichowska B, Rę kas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

\* cited by examiner

EYE THERAPY SYSTEM

CROSS REFERENCE TO RELATED APPLICATIONS

This application claims priority to U.S. Provisional Application No. 61/098,489, filed Sep. 19, 2008, and U.S. Provisional Application No. 61/101,503, filed Sep. 30, 2008, the contents of these applications being incorporated entirely herein by reference.

BACKGROUND OF THE INVENTION

1. Field of the Invention

The invention pertains to the field of keratoplasty and, more particularly, to the operation of a device configured to treat one or more eye disorders by applying energy in multiple steps to cause corrective reshaping of an eye feature.

2. Description of Related Art

A variety of disorders, such as myopia, hyperopia, and presbyopia, involve refractive disorders in the eye. For example, with myopia, the shape of the cornea causes the refractive power of an eye to be too great and images to be focused in front of the retina, affecting visualization of far objects. Meanwhile, hyperopia is a refractive condition characterized by a flattened corneal curvature or short eyeball that focuses light to a point behind the retina and prevents visualization of near objects.

In addition to glasses and contact lenses, invasive surgical procedures, such as laser-assisted in-situ keratomileusis (LASIK), may be employed to reshape the cornea to treat disorders, such as myopia and hyperopia. Such surgical procedures, however, typically require a healing period after surgery. In addition, such surgical procedures may result in complications, such as problems related to the lamellar flap or dry eye syndrome caused by the severing of corneal nerves. Moreover, LASIK is an ablative, subtractive procedure and, as such, is not ideal for treating hyperopia, because steepening the cornea to treat hyperopia requires the removal of a substantial amount of peripheral tissue.

Conductive keratoplasty (CK), the current surgical standard of care for hyperopia treatment, is an invasive procedure that involves applying low-level, radio frequency (RF) energy through needle electrodes placed in a circular pattern on the outer part of the cornea. The RF energy causes corneal fibers to shrink where applied, causing central steepening of the cornea. CK does not necessitate tissue removal but suffers from limits to the predictability of the outcomes and the durability of the results, in addition to the possibility of astigmatism induction from improper electrode placement.

Unlike hyperopia and myopia which are refractive dysfunctions caused by eyeball geometry and corneal shape, presbyopia is a refractive disorder that is caused by age-related changes in the crystalline lens and results in the loss of accommodation, i.e., an impaired ability to focus on near objects. In addition to glasses and contact lenses, three main surgical methods exist for the treatment of this disorder: (1) multifocal intraocular lenses (MIOLs), (2) monovision treatment employing LASIK or CK, and (3) multifocal LASIK (PresbyLASIK). The latter two are variations on refractive surgeries in current practice, while the former is the replacement of the natural lens with an artificial alternative.

Monovision treatment provides both near and distance vision by adapting one eye for distance, usually the dominant eye, and a second eye for near vision. Both LASIK and CK may be employed for monovision treatment. The monovision approach is not without limitations, however, as not all patients tolerate having each eye focused on a different plane. Indeed, it is recommended that patients undergo careful personality screening and experience simulated monovision with contact lenses before proceeding with refractive surgery. Those who do get the treatment have a 60-70% success rate with the main limitations being problems with night driving, impairment of stereopsis, and inability to focus on objects at an intermediate distance (e.g., computer monitors). These limitations have motivated the development of multifocal correction techniques, with the aim of preserving binocular vision.

The most common refractive surgery technique for bilateral multifocal correction is PresbyLASIK, a modified version of LASIK which treats presbyopia by creating both near and distance vision in a single cornea. Originally, multifocal laser ablation used photorefractive keratectomy (PRK), however, few modern approaches use this surface ablation technique anymore, with one reviewer suggesting that this is most likely due to complications with epithelial regrowth. LASIK avoids these compensatory reactions. Three different LASIK ablation profiles that induce both near and distance vision are described in the literature, each with their own advantages and disadvantages.

Transitional PresbyLASIK is characterized by an intentional decentration of the near vision zone to create a pattern reminiscent of a bifocal spectacle. However, the technique was not widely accepted by the surgical community as it required the creation of a significant vertical coma in the cornea and most surgeons were not comfortable with this approach.

Central PresbyLASIK steepens the center of the cornea to provide near vision, while flattening the periphery to provide distance vision. The ablative nature of LASIK makes this approach particularly attractive as it requires the removal of the least amount of tissue. However, this technique is prone to inducing corneal aberrations.

Peripheral PresbyLASIK produces the inverse zonal arrangement with distance vision through the central cornea and near vision through the periphery. This method potentially provides the greatest amount of pseudoaccomodation. However, because LASIK is subtractive, a significant amount of corneal tissue must be removed.

Moreover, a significant drawback of current multifocal treatments such as PresbyLASIK is the discontinuity of corneal curvature at the boundary of the near and distance vision zones. This results in instantaneous differences in refractive power that can cause visual aberrations such as starbursts and halos, adversely affecting night vision. Another drawback is the absence of an intermediate distance vision zone, resulting in an inability to focus on objects at an intermediate distance.

SUMMARY OF THE INVENTION

In view of the foregoing, there is a need for an eye therapy that precisely and accurately reshapes the cornea to treat a variety of refractive disorders, such as myopia, hyperopia, and presbyopia, in a wide range of patients without the disadvantages of the approaches described previously. Moreover, there is a need for an eye therapy that treats a combination of these disorders. For example, there is a strong clinical need for a refractive procedure which can treat the presence of both hyperopia and presbyopia, without compromising the structural integrity of the cornea, sacrificing the depth of field associated with natural binocular vision, or creating sudden discontinuities in corneal curvature. To address these and other needs, embodiments according to aspects of the present invention apply energy to the cornea in multiple precise and measured steps to achieve a desired change in the shape of the cornea.

For example, a method applies an initial amount of energy to an eye feature and then determines whether or not the specified shape change has been achieved. The energy causes the targeted area of the eye to conform to a new shape. If the specified amount of reshaping has not been achieved, then the method applies one or more additional amount of energy to the eye feature to cause further reshaping.

In another example, a method applies an initial amount of energy to an eye feature according to an initial pattern at an initial location. The method determines whether a specified amount of reshaping has been achieved due to the application of energy to the eye feature. If the specified amount of reshaping has not been achieved, the method applies one or more additional amounts of energy according to one or more additional patterns and/or locations to cause further reshaping.

Accordingly, the cornea may be shaped more precisely and accurately according to incremental and measured steps using measurements of the results of each application of energy as feedback. Moreover, the cornea may be shaped according to varying amounts of energy in varying patterns and/or at varying locations to achieve a customized reshaping of the cornea to address the specific needs of an individual patient.

In a further example, a method may form lesions that provide multifocal reshaping to treat more than one disorder. For example, one step may form a substantially circular lesion to flatten a first portion of the cornea to treat presbyopia, while another step may form a substantially circular and concentric lesion having a greater diameter to steepen a second portion of the cornea to treat hyperopia. Advantageously, continuous transitional regions are formed relative to the reshaped portions to provide vision for intermediate distances as well. Thus, this multifocal treatment may be employed to treat a patient having both hyperopia and presbyopia.

These and other aspects of the present invention will become more apparent from the following detailed description of the preferred embodiments of the present invention when viewed in conjunction with the accompanying drawings.

DESCRIPTION

Figure 1:
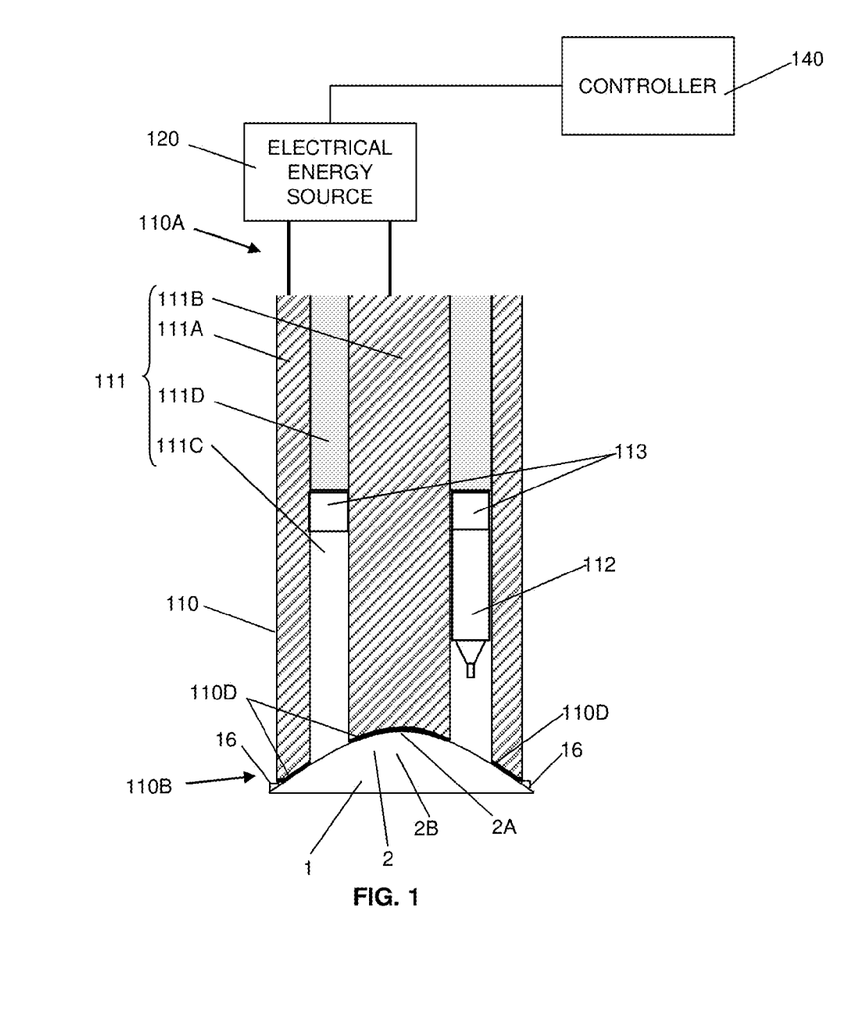
FIG. 1 illustrates an example system for applying energy to a cornea of an eye to cause reshaping of the cornea.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply energy to the cornea 2, which is positioned at the distal end 110B. In particular, the electrical energy source 120 may include a microwave oscillator for generating microwave energy. For example, the oscillator may operate at a microwave frequency range of 400 MHz to 3000 MHz, and more specifically at a frequency of around 915 MHz or 2450 MHz. As used herein, the term "microwave" corresponds to a frequency range from about 10 MHz to about 10 GHz.

As further illustrated in FIG. 1, the electrical energy conducting element 111 may include two microwave conductors, or electrodes, 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the outer conductor 111A. With the inner passage, the conductor 111A may have a substantially tubular shape. The outer conductor 111A and inner conductor 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 110B, where the cornea 2 is positioned.

The outer diameter of the inner conductor 111B is preferably larger than the pupil. In general, the outer diameter of the inner conductor 111B may be selected to achieve an appropriate change in corneal shape, i.e., keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

A controller 140 may be employed to selectively apply the energy any number of times according to any predetermined or calculated sequence. The controller 140 may include a computer device to control the application of energy according to instructions provided via a computer-readable storage medium. In addition, the controller 140 may include a monitor and keyboard, or other user interface devices for receiving instructions from an operator.

Depending on the instructions, the energy may be applied for any length of time. Furthermore, the magnitude of energy being applied may also be varied. Adjusting such parameters for the application of energy determines the extent of changes that are brought about within the cornea 2. The system attempts to limit the changes in the cornea 2 to an appropriate amount of shrinkage of collagen fibrils in a selected region. When employing microwave energy to generate heat in the cornea 2, for example with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 110B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 51 μm (0.002 inches). In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic, such as polyurethane and silastic, or nonelastic, such as Teflon® and polyimides. The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

The system of FIG. 1 is provided for illustrative purposes only, and other systems may be employed to apply energy to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference. As described in U.S. patent application Ser. No. 12/208,963, the embodiments described herein may all employ sensors to measure physical variables of the eye. For example, in one embodiment, FIG. 1 depicts a plurality of sensors 16 which are discretely positioned at and about the distal end 110B of the applicator 110. In other embodiments, sensors may be more broadly incorporated into a surface at the distal end of the applicator, such as the dielectric layer 110D. Typically, the sensors are placed in contact with the cornea and provide measurements for various areas of the cornea. In general, the sensors may include devices that are formed as parts of the applicator and/or external devices that are separate from the applicator. The sensors may be microelectronic devices, including, but not limited to, infrared detectors that measure temperature, thin film or microelectronic thermal transducers, mechanical transducers such as a piezoresistive or piezoelectric devices, or force-sensitive quartz resonators that quantify corneal elongation or internal pressure. In general, the sensors may provide information that is used to prepare the systems before treatment, provide feedback during treatment to ensure proper application of treatment, and/or measure the results of the treatment.

As described in U.S. patent application Ser. No. 12/208,963, a cooling system may be employed in combination with the applicator 110 to apply coolant to the cornea 2 and determine how the energy is applied to the cornea 2. For example, the applicator 110 may include, internally or externally, at least one coolant delivery element 112 in fluid communication with a coolant supply 113, or reservoir. The coolant delivery element 112 delivers a coolant, or cryogen, from the coolant supply 113 to the distal end 110B of the applicator 110. In some embodiments, the coolant may be applied more directly to the dielectric layer 110D disposed along the distal end 110B, if the dielectric layer 110D substantially encloses the distal end 110B of the applicator 110. In general, the applicator may be employed to apply coolant to selectively cool the surface 2A of the cornea 2 positioned at the distal end 110B. The delivery of coolant from the coolant delivery element 112 toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

Figure 2:
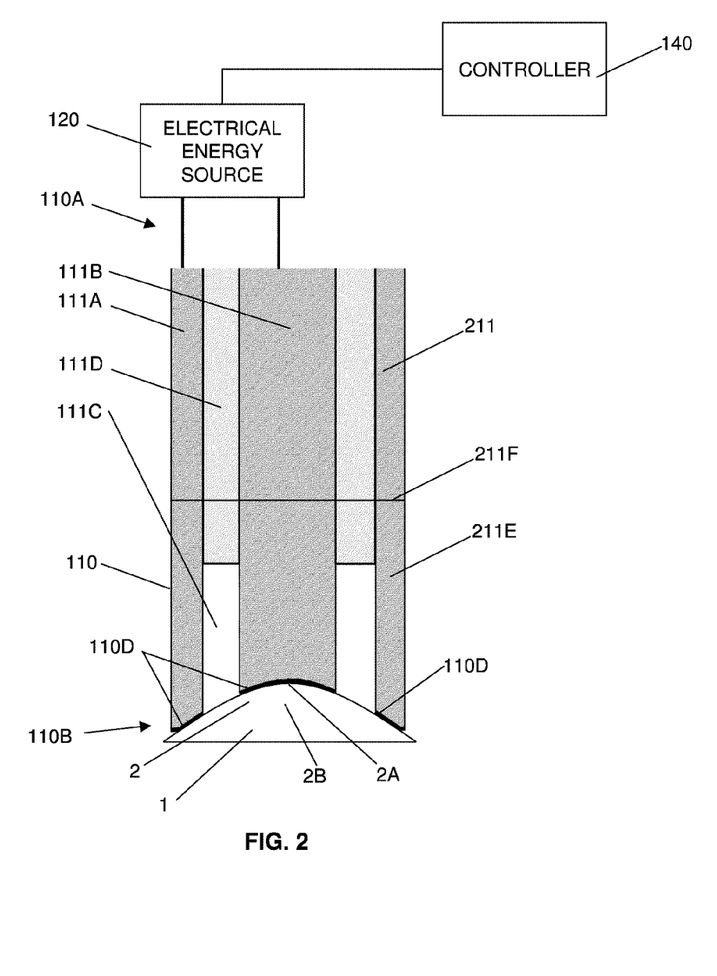
FIG. 2 illustrates another example system for applying energy to a cornea of an eye to cause reshaping of the cornea.

In addition, as described in U.S. patent application Ser. No. 12/208,963, the applicator 110 may include replaceable components. In particular, as shown in FIG. 2, the applicator 110 may include a replaceable end piece 211E that defines the energy conducting element 211 at the distal end 110B. The end piece 211E is removably attached at a connection 211F with the rest of the energy conducting element 211 using any conductive coupling that permits energy to be sufficiently conducted to the cornea 2. For example, the end piece 211E may be received via threaded engagement, snap connection, other mechanical interlocking, or the like. Accordingly, end pieces 211E having different dimensions and/or shapes may employed with a single applicator 110. As such, a single applicator 110 may deliver energy to the cornea 2 according to varying patterns defined by replaceable end pieces 211E with different dimensions. Furthermore, the end pieces 211E may be disposable after a single use to promote hygienic use of the applicator 110. Other aspects of end pieces are employable with the applicator 110 are described, for example, in U.S. patent application Ser. No. 12/018,473, filed Jan. 23, 2008, the contents of which are incorporated herein by reference.

In operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A, though a thin interposing dielectric layer 110D may be disposed between the conductors 111A and 111B and the corneal surface 2A. Accordingly, direct contact helps ensure that the pattern of microwave heating in the corneal tissue has substantially the same shape and dimension as the gap 111C between the two microwave conductors 111A and 111B.

Prior to positioning of the applicator 110 in contact with the corneal surface 2A, the corneal surface 2A may be scanned to make a topographical map showing the shape and curvature of the surface of the cornea. Then, with the conductors 111A and 111B positioned flush with the corneal surface 2A, the treatment may apply durations of microwave pulses to heat and reshape collagen and coolant pulses to protect the corneal surface. In one aspect, the treatment attempts to shrink the collagen in the cornea 2 and form a precisely controlled annular lesion in approximately the upper 150 μm of the stroma. The microwave treatment raises the temperature of an annulus, just below the surface of the cornea, to a temperature in the range of approximately 60 to 75° C. Using evaporative surface cooling techniques, the system cools the surface of the cornea during treatment to isolate and protect the epithelium and Bowman's membrane from microwave heating. Thus, the treatment is noninvasive, as there is no cutting or penetration of the eye. In one example application, the applicator 110 predictably flattens the central cornea to achieve mild-to-moderate myopic correction (−0.5 to −3.5 diopters, D) without compromising the biomechanical integrity of the cornea.

Accordingly, embodiments according to aspects of the present invention may use microwave energy emitted from the applicator 110, e.g., in a ring-shaped pattern, around the pupil to shrink stromal collagen and modify the dioptric power of the cornea, while a cooling system acts on the corneal surface to minimize thermal damage to the epithelium. In particular, electric field lines form a fringing pattern that extends into the corneal stroma to a depth determined by the applied power and applicator geometry. This electric field causes the polar water molecules to align themselves with the field; the rapid reversal of the sinusoidally-varying field causes frictional heating by these molecules as they rotate in place. This effect does not require a conduction current to flow through a point of electrical contact between a conductor and tissue; heating is caused by a displacement current.

Figure 3A:
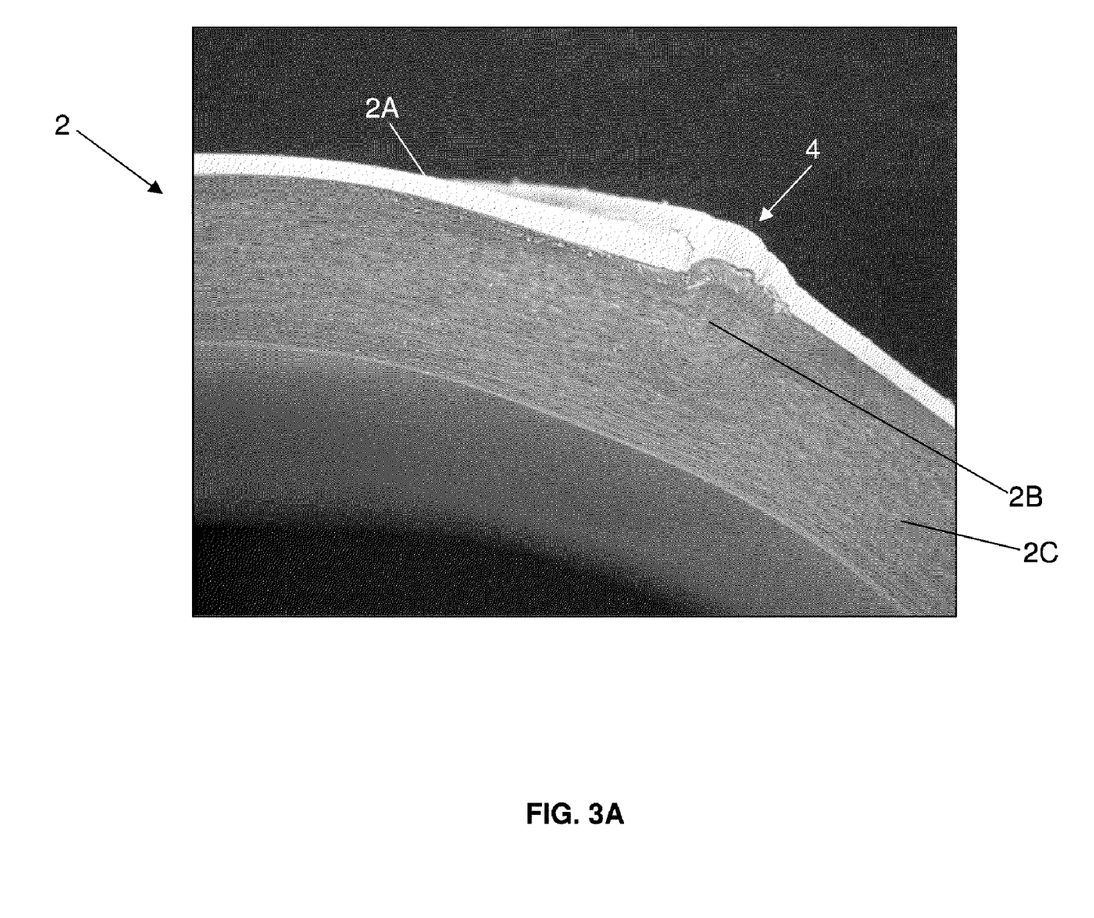
FIG. 3A illustrate a high resolution image of a cornea after energy has been applied.
Figure 3B:
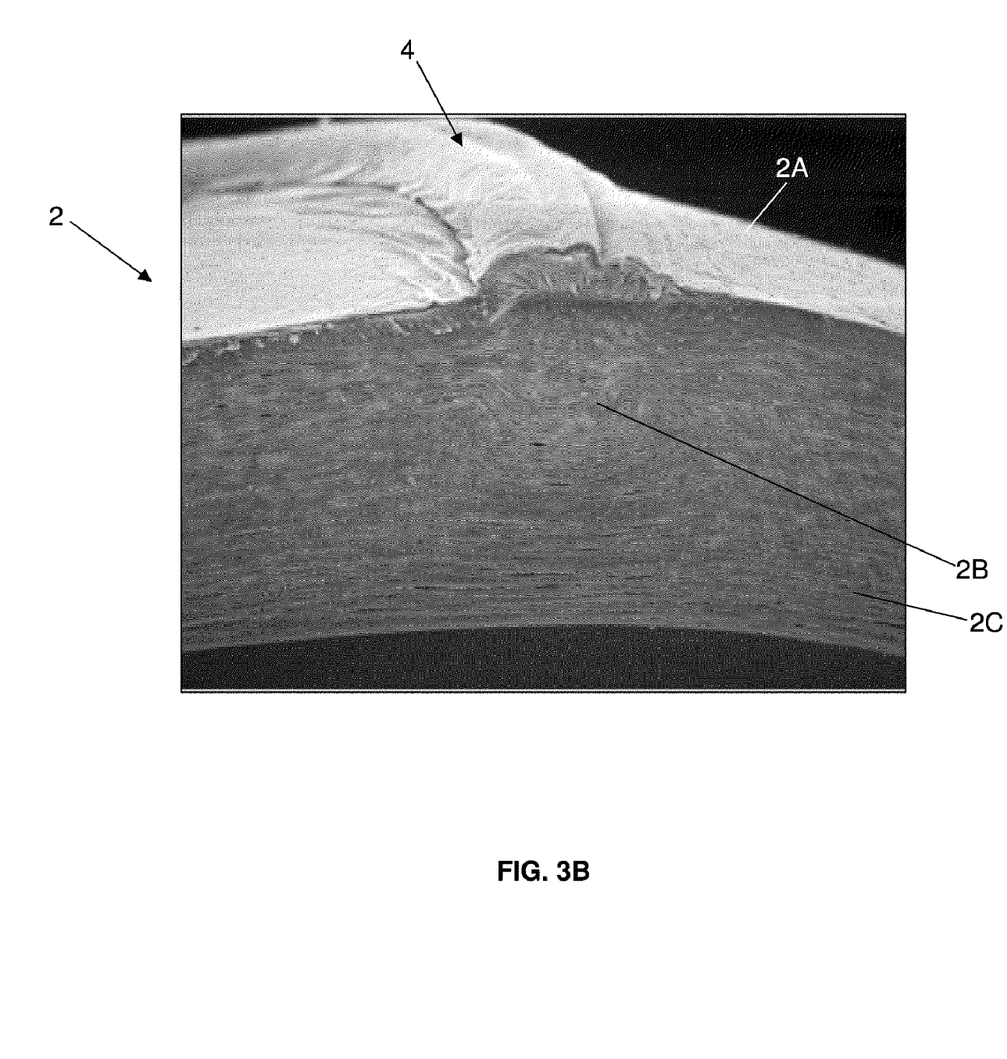
FIG. 3B illustrate another high resolution images of the cornea of FIG. 3A.

FIGS. 3A-D illustrate an example of the effect of applying heat to corneal tissue with a system for applying heat, such as the systems illustrated in FIG. 1 and FIG. 2. In particular, FIGS. 3A and 3B illustrate high resolution images of cornea 2 after heat has been applied. As FIGS. 3A and 3B show, a lesion 4 extends from the corneal surface 3A to a mid-depth region 3B in the corneal stroma 3C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 3C:
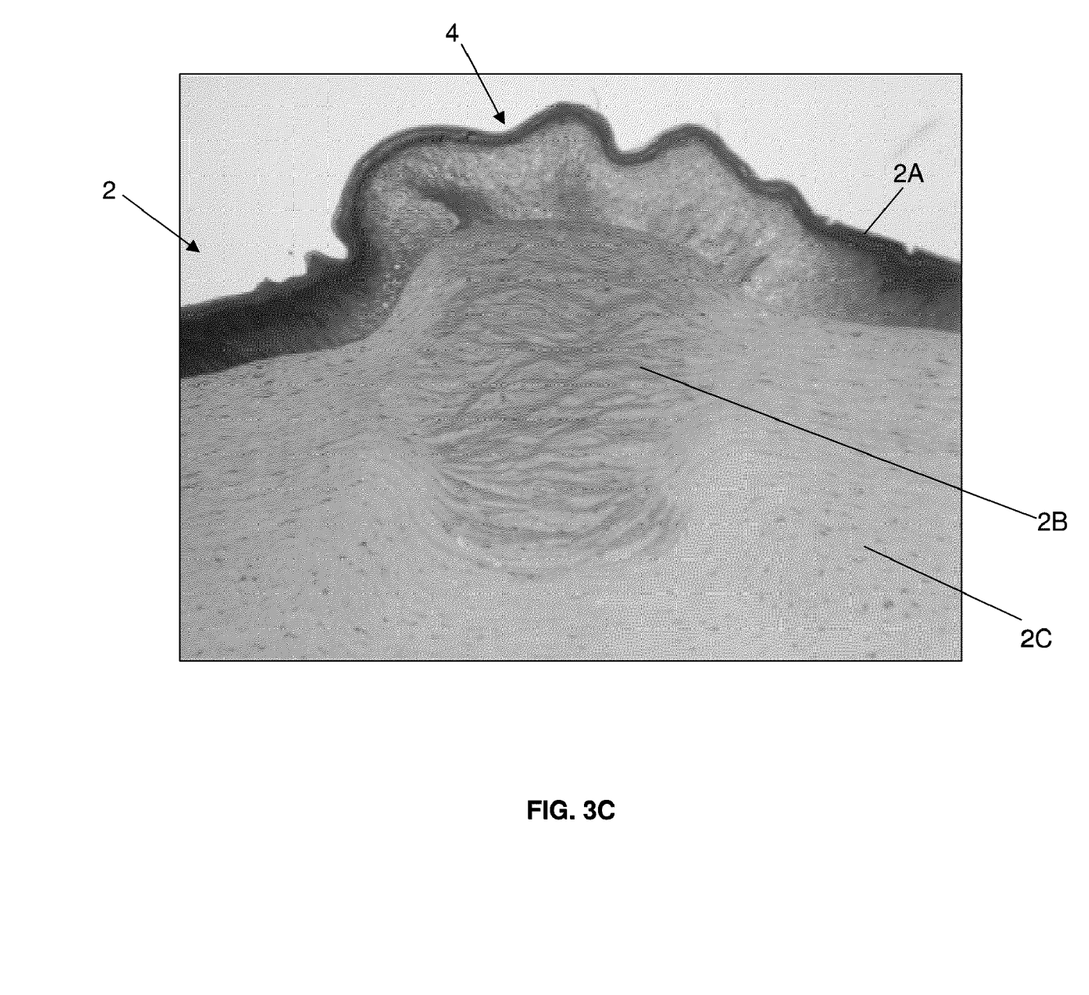
FIG. 3C illustrates a histology image of the cornea of FIG. 3A.
Figure 3D:
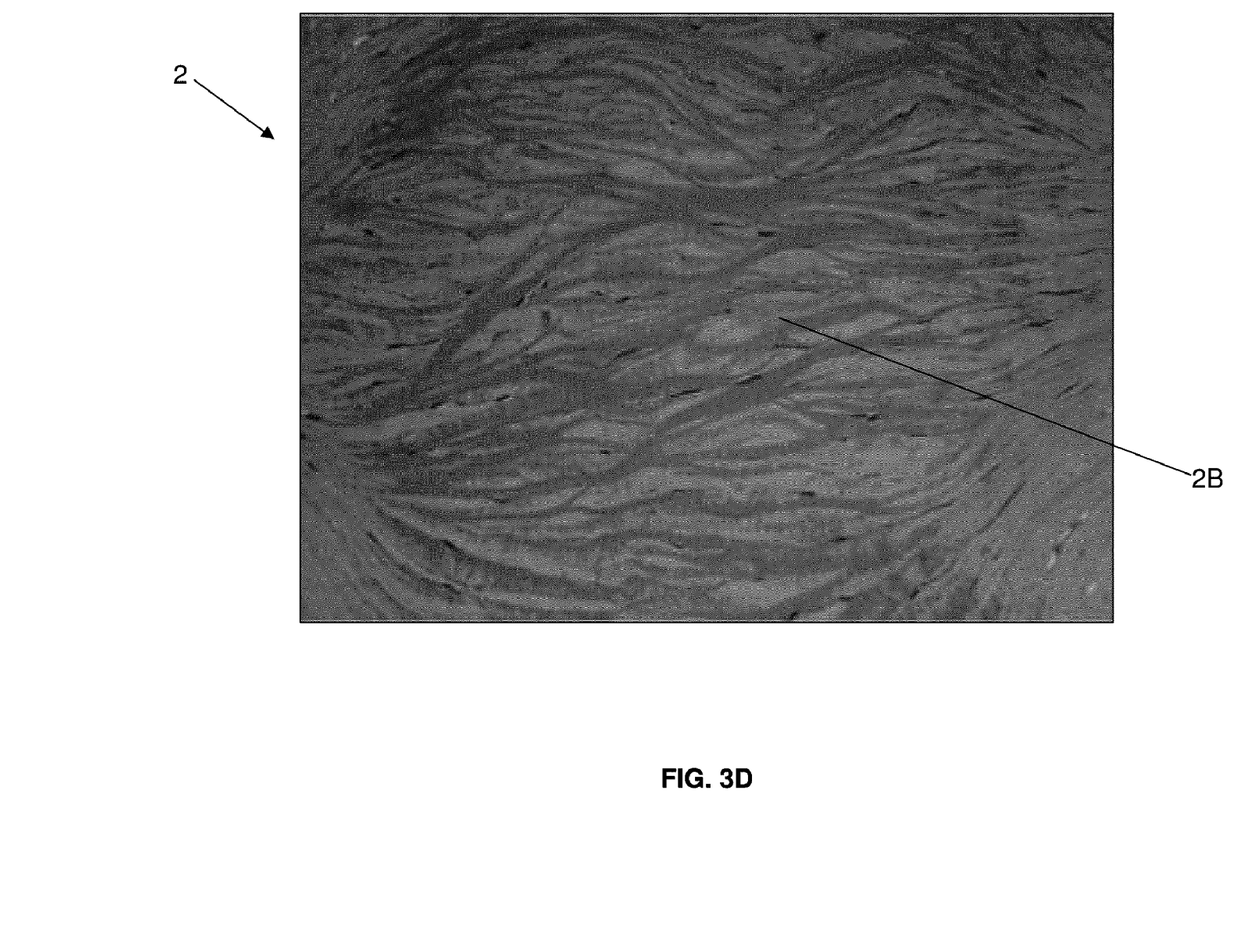
FIG. 3D illustrates another histology image of the cornea of FIG. 3A.

As further illustrated in FIGS. 3A and 3B, the changes in corneal structure are localized and limited to an area and a depth specifically determined by an applicator as described above. FIGS. 3C and 3D illustrate histology images in which the tissue shown in FIGS. 3A and 3B has been stained to highlight the structural changes induced by the heat. In particular, the difference between the structure of collagen fibrils in the mid-depth region 3B where heat has penetrated and the structure of collagen fibrils outside the region 3B is clearly visible. Thus, the collagen fibrils outside the region 3B remain generally unaffected by the application of heat, while the collagen fibrils inside the region 3B have been rearranged and formed new bonds to create completely different structures. In other words, unlike processes, like orthokeratology, which compress areas of the cornea to reshape the cornea via mechanical deformation, the collagen fibrils in the region 3B are in an entirely new state.

Clinical studies involving a system similar to that in FIG. 1 have been conducted for the treatment of spherical myopia. In particular, the clinical studies evaluated the safety and the efficacy correcting spherical myopia ranging up to 6.0 D. The study enrolled 25 subjects, 16 white females and 9 white males, and treatments were performed on 25 eyes. Enrollment criteria included 1.0 D or more of spherical equivalent myopia and the availability of subjects for follow-up examinations for 12 months post procedure. Exclusion criteria included history of herpes keratitis, autoimmune disease or diabetes mellitus, etc.

An aim of the clinical studies was to meet the safety endpoints, which require less than 10% of the treated eyes (1) losing more than 2 lines of best spectacle correction visual acuity (BSCVA), (2) manifesting a refractive astigmatism of greater than 2.0 D, or (3) undergoing any adverse device effects. Another aim was to meet the efficacy endpoint which requires a refractive predictability of at least 50% of eyes achieving a manifest refraction spherical equivalent (MRSE) of ±1.00 D of the attempted treatment.

In the results of the clinical studies, all the safety endpoints were met with no eyes losing more than 2 lines of BSCVA or having astigmatism of 2.00 D. At one month, 80% of subjects were within ±1.00 D of intended correction, 87% had UCVA≦20/40, no subjects lost more than 2 lines of BSCVA, and 60% exhibited improved contrast sensitivity. The results of the studies showed a predictable relationship between the energy delivered to the eye and the refractive correction achieved. Furthermore, these studies with human patients demonstrated that the post-treatment anterior corneal surface has no sudden inflections. This indicated that, when combining a hyperopia and myopia treatment on a single eye, it is possible to create a transitional region providing intermediate distance vision as well.

Figure 4:
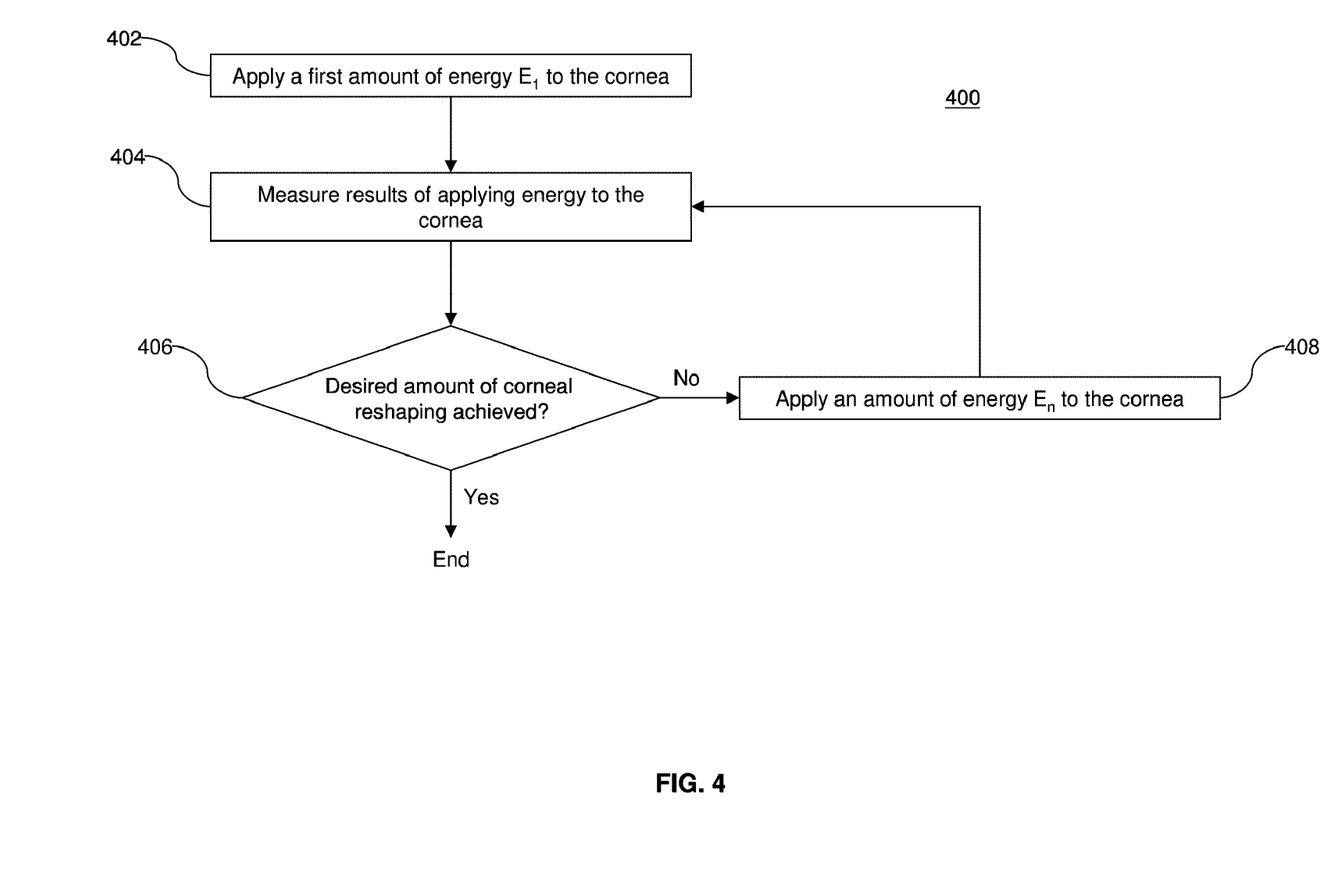
FIG. 4 illustrates an example multi-step operation of a system such as that of FIG. 1 according to aspects of the present invention.

FIG. 4 illustrates a method 400 for operating a system similar to that of FIG. 1. For example, the applicator 110 and the controller 140 described previously may be employed to deliver energy to the cornea 2 of the eye 1 according to the method 400. In particular, the method 400 incrementally applies heat to the cornea 2 in precise and measured steps to achieve a desired change in the shape of the cornea 2. In step 402, a first amount of energy $E_1$ is delivered to the cornea 2. The energy $E_1$ may be delivered according to any power level for any amount of time and any number of pulses. Although the application of energy $E_1$ causes changes in corneal structure, the changes may not be sufficient to achieve the desired amount corneal reshaping. For instance, the reshaping may not completely correct a myopic condition. Thus, the results of applying energy $E_1$ in step 402 may be intraoperatively measured in step 404. In some embodiments, the measurement in step 404 may be achieved with a keratometer, topographer, autorefractor, aberrometer, interferometer, or any instrument that can measure the shape of the corneal surface or the refractive power of the eye. In step 406, the measurement of step 404 is compared to the desired amount of corneal reshaping, e.g., a threshold measurement. If the desired amount of corneal reshaping has not been achieved, another amount of energy $E_n$ may be applied in step 408 to cause further changes in corneal structure. The amount of energy $E_n$ depends at least on the results measured in step 404. The energy $E_n$ represents any amount of energy, which may also be delivered according to any power level for any amount of time and any number of pulses. Steps 404, 406, and 408 may be repeated iteratively until the corneal is reshaped as desired. For instance, the energy $E_n$ may be applied one or more times until any residual myopia is removed.

In some embodiments of method 400, the application of energy $E_1$ in step 402 may purposely under-treat the cornea 2 so that further corneal reshaping is required through the application of the energy $E_n$ in step 408. Accordingly, the cornea 2 may be shaped more precisely and accurately according to incremental and measured steps using measurements of the results of each application of energy as feedback.

Figure 5:
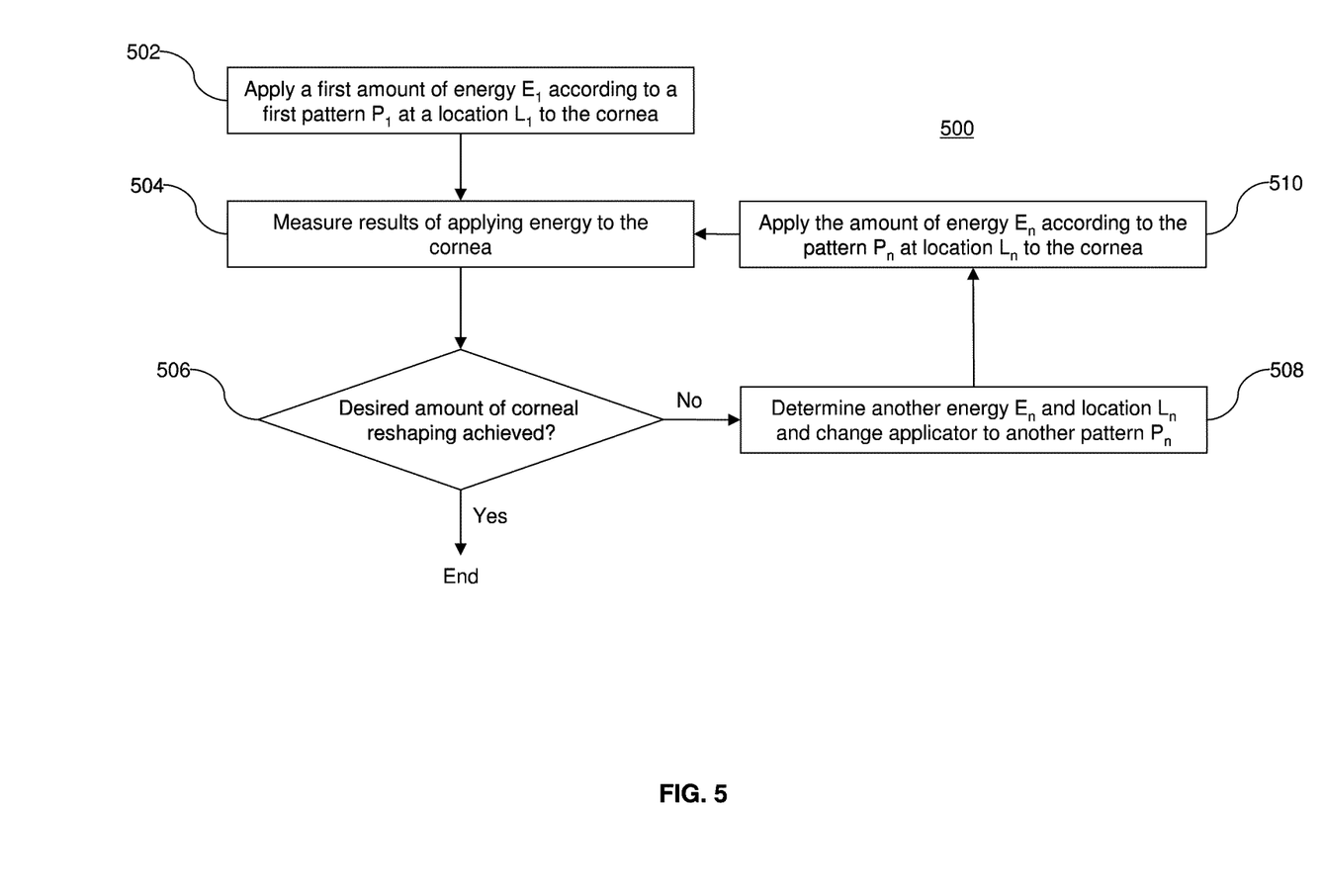
FIG. 5 illustrates another example multi-step operation of a system such as that of FIG. 1 according to aspects of the present invention.

FIG. 5 illustrates another method 500 for operating a system similar to that of FIG. 1. For example, the applicator 110 and the controller 140 described previously may be employed to deliver energy to the cornea 2 of the eye 1 according to the method 500. In particular, the method 500 achieves a desired change in the shape of the cornea 2 by incrementally applying energy to the cornea 2 in precise and measured steps according to different patterns and/or at different locations of the cornea 2. As described previously, the applicator 110 may employ more than one end piece 111E as shown in FIG. 2, each having a different dimension and/or shape to deliver energy to the cornea 2 according to varying patterns. As such, each incremental step may employ a different end piece 111E with the applicator 110. Alternatively, rather than employ replaceable end pieces, the entire applicator 110 may be replaced for each application of energy.

Referring again to FIG. 5, a first amount of energy $E_i$ is delivered to the cornea 2 according to a first pattern $P_1$ at a first location $L_1$ in step 502. The energy $E_1$ may be delivered according to any power level for any amount of time and any number of pulses. The amount of energy applied to the cornea 2 determines the lesion depth and thus the resulting shape change in the cornea 2. Accordingly, the first amount of energy $E_1$, the first pattern $P_1$, and the first location $L_1$ determine the depth, shape, and location of the first lesion in the cornea 2. Although the application of energy $E_1$ with pattern $P_1$ at location $L_1$ causes changes in corneal structure, the changes may not achieve the desired cornea reshaping. Thus, the results of applying energy $E_1$ in step 402 are intraoperatively measured in step 504. In some embodiments, the measurement in step 504 may be achieved with a keratometer, topographer, autorefractor, aberrometer, interferometer, or any instrument that can measure the shape of the corneal surface or the refractive power of the eye.

In step 506, the measurement of step 504 is compared to the desired amount of corneal reshaping, e.g., a threshold measurement. If the desired amount of corneal reshaping has not been achieved, another amount of energy $E_n$ as well as another pattern $P_n$ and/or location $L_n$ are determined in step 508 according to the results measured in step 504. The energy $E_n$ may then be applied in step 510 with the pattern $P_n$ and/or at location $L_n$ to cause further changes in corneal structure. In particular, the amount of energy $E_n$, the first pattern $P_n$, and the first location $L_n$ determine the depth, shape, and location of a subsequent lesion in the cornea 2. The energy $E_n$ represents any amount of energy, which may also be delivered according to any power level for any amount of time and any number of pulses. Steps 504, 506, 508, and 510 may be repeated iteratively until the corneal is reshaped as desired. For instance, the energy $E_n$ may be applied one or more times according to varying patterns $P_n$ and/or locations $L_n$ until the desired shape correction is achieved. The energy $E_n$, patterns $P_n$, and/or locations $L_n$ at each step are selected according to the changes to the refractive state of the eye caused by previous applications of energy. Accordingly, the cornea 2 may be shaped more precisely and accurately according to incremental and measured steps using measurements of the results of each application of energy as feedback.

It has been observed that when the cornea is flattened with a substantially circular pattern, for example, most of the flattening of the cornea occurs where the pattern is actually applied, and less flattening occurs at the center and outside the pattern. The amount of residual myopia, for example, remaining at the center of the pattern is a function of the diameter of the pattern and the initial refractive state of the cornea. According to aspects of the present invention, it is possible to select an additional patterns of different diameters for subsequent applications of energy to produce a customized reshaping of the cornea.

Although some embodiments may employ a measurement step, e.g., step 504, before applying another amount of energy $E_n$, it is understood that the result of applying another amount of energy $E_n$ with the pattern $P_n$ and/or at location $L_n$ may be relatively predictable, so that a measurement step is not necessary. As such, it may be possible to select a priori the energy conducting elements for delivering energy according particular patterns P without requiring a measurement step. In general, the cornea may be reshaped in multiple steps according to varying amounts of energy in varying patterns and/or at varying locations to achieve a customized reshaping of the cornea to address the specific needs of an individual patient.

Figure 6:
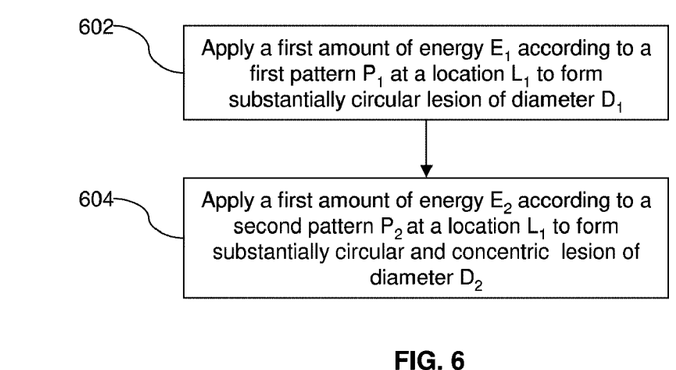
FIG. 6 illustrates yet another example multi-step operation of a system such as that of FIG. 1 according to aspects of the present invention.
Figure 7:
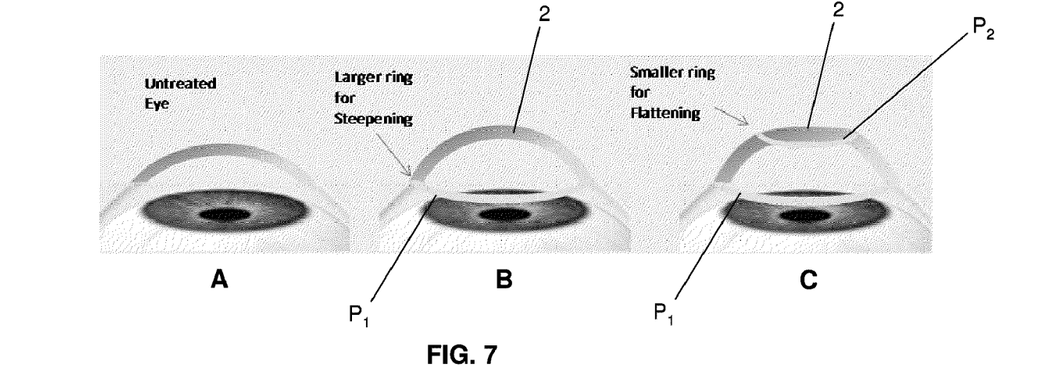
FIG. 7 illustrates the results of applying the multi-step operation of FIG. 6 according to aspects of the present invention.

In an example implementation, embodiments produce a multifocal correction by applying microwave heating to produce a small diameter lesion within a concentric larger diameter lesion. In particular, in step 602, energy $E_1$ is applied to the cornea 2 employing an applicator 110 with a first diameter $D_1$ (pattern $P_1$) to produce a substantially circular lesion corresponding to a first diopter. In subsequent step 604, energy $E_2$ is applied to the cornea according to employing an applicator 110 with a second diameter $D_2$ (pattern $P_2$) to produce another substantially circular lesion corresponding to another diopter. In particular, the diameter $D_1$ is larger than the diameter $D_2$. Referring to FIG. 7, panel A illustrates an untreated eye; panel B illustrates the application of the pattern $P_i$ of diameter $D_i$ to form a lesion that steepens an aspect of the cornea 2; and panel C illustrates the further application of a pattern $P_2$ of diameter $D_2$ to form a lesion that flattens another aspect of the cornea 2. In this example, the lesions may be concentric about the corneal apex. Depending on how far from the corneal apex the lesion is formed, the central region of the cornea can be either flattened or steepened. Therefore, by forming two lesions of different diameters and lesion depths to the same cornea, a prolate multifocal cornea is created. For example, one particular treatment may employ electrode diameters on the order of 4.0 mm for flattening and 8.0 mm for steepening, allowing 1.9 mm radial spacing between the lesions. Thus, embodiments according to aspects of the present invention provide a corrective treatment that produces continuously graded prolate corneas with multifocal zones for both near and distance vision. Advantageously, the absence of sudden inflections in the corneal surface when two lesions are applied provides a transitional region that allows intermediate distance vision as well.

Unlike LASIK, for example, application of treatment according to aspects of the present invention does not affect the biomechanical integrity of the cornea. The dimensional stability of the cornea, of primary importance for maintaining clear vision, results from the cornea's mechanical resiliency and is directly attributable to the composition and structure of the extracellular matrix of the stroma, the connective tissue layer that comprises most of the cornea's thickness and which is made up of several hundred superimposed stromal lamellae.

Unlike CK, application of treatment according to aspects of the present invention is predictable and repeatable in part because of the single continuous pattern, e.g., a single continuous circular lesion versus a series of spots to form a circular pattern. It can also be used to create true multifocal corrections by creating smoothly graded corneal curvatures that transition from near to distance vision while providing intermediate distances in between.

In addition, application of treatment according to aspects of the present invention offers the inherent advantages of a peripheral PresbyLASIK zonal arrangement (distance vision via the center of the cornea, near vision via the periphery of the cornea) but does not require any tissue ablation. The approach allows graded flattening or steepening of the central and peripheral regions, producing multifocal zones for both near and distance vision. Because the prolate shape of the cornea is maintained, the full range of intermediate distance is also provided and the risk of visual aberrations is minimized.

Ex vivo studies were performed to evaluate the feasibility of a system similar to that of FIG. 1 to effect corneal steepening (as a basis for hyperopia correction) and concentric lesions (as a basis for multifocal correction). Specifically, hyperopia correction requires the ability to induce corneal steepening. Using a wavefront abberometer (iTrace, Tracey Technologies, Houston, Tex.) porcine eyes were screened for hyperopia (i.e. spherical>0.0 D). Six were selected and measured three times to establish a pre-treatment refraction. All eyes were then were treated using an applicator having a 6.0 mm diameter, 200 µm thickness, and an energy of approximately 4 J. Finally, each eye was measured three times with the wavefront abberometer to establish a post-treatment refraction. Using the equations shown below:

$$Seq = S + C/2 \quad (1)$$

$$C+ = 0.5C \cos(2A) \quad (2)$$

$$C\times = 0.5C \sin(2A) \quad (3)$$

where S is spherical component, C is the cylindrical component, and A is the axis, the induced correction was calculated. The results showed an average steepening of 1.33±0.84 D and very little induced astigmatism (C+−0.09±0.33 D; C×0.19±0.20 D). Five of the six eyes showed steepening of at least 1.0 D. These results demonstrated the feasibility of inducing corneal steepening according to aspects of the present invention, the effects of which would be enhanced with an even larger diameter electrode.

As described further below, dual concentric lesions may be formed according to a multifocal application of the present invention to produce desired corneal reshaping. Accurate placement of thermal lesions may be an important aspect for treatment involving dual concentric lesions. To evaluate the feasibility of this approach, dual lesions were created on a single porcine eye with an applicator having a 5.0 mm diameter, followed by an applicator having a 5.5 mm diameter and 200 µm thickness. The eye was then studied with Scheimpflug imaging (Galilei Dual Scheimpflug Analyzer, Zeimer Ophthalmic System AG, Allmendstrasse, CH), demonstrating excellent concentricity. To avoid overlapping lesions, a concentricity of 150 µm was maintained, accounting for the 100-200 µm range of lesion thickness. These ex vivo results demonstrate the feasibility of multifocal treatment according to aspects of the present invention. For example, one particular treatment may employ outer conductor diameters on the order of 4.0 mm for flattening and 8.0 mm for steepening, allowing 1.9 mm radial spacing between the lesions. Proper positioning of the applicator makes acceptable concentricity possible.

In general, the amount of energies $E_1$ and $E_n$ as well as patterns $P_1$ and $P_n$ and locations $L_1$ and $L_n$ in the examples above may be determined according to patient characteristics, including, but not limited to, age, gender, corneal thickness, and other similar factors that affect how corneal changes may be induced. Data relating to such factors and corresponding energies $E_i$ and $E_n$ as well as patterns $P_i$ and $P_n$ and locations $L_i$ and $L_n$ may be compiled from clinical observations and may be reduced to a nomogram, look-up table, or the like. This compiled data may then serve as a guide for determining the parameters for providing treatments according to aspects of the present invention.

An understanding of the cornea's biomechanics is important to the development of predictive models of refractive procedures. A computational biomechanics model of the cornea's response to the embodiments described herein may be developed to guide the design, fabrication, and testing of microwave electrodes for both hyperopic and multifocal correction. The acts for developing such a model may include, for example:

Developing a finite element analysis (FEA) structural model of the cornea's response, including:
1. Modeling flattening of the central cornea in response to a small diameter (<5 mm) thermal lesion, validating and refining the model using patient data from myopia studies.
2. Extending the model to steepening of the central cornea in response to a large diameter (>5 mm) thermal lesion and continuously graded curvature in response to combined small and large diameter thermal lesions.
3. Based on these numerical studies, developing CAD models of candidate electrode configurations.

Fabricating feasibility prototypes and characterize ex vivo performance of large diameter electrodes in producing a steepening hyperopic treatment with porcine eyes, including developing a nomogram correlating treatment parameters (e.g., energy E, pattern P, location L) with target diopters of hyperopic correction.

Characterizing ex vivo performance of combined small and large diameter electrodes in producing a continuously graded corneal curvature, including developing a nomogram correlating treatment parameters with corneal shape change.

Although the embodiments described herein may apply energy to the cornea according to an annular pattern defined by an applicator such as the applicators 110 and 210, the pattern in other embodiments is not limited to a particular shape. Indeed, energy may be applied to the cornea in non-annular patterns. Examples of the non-annular shapes by which energy may be applied to the cornea are described in U.S. patent Ser. No. 12/113,672, filed on May 1, 2008, the contents of which are entirely incorporated herein by reference.

While the present invention has been described in connection with a number of exemplary embodiments, and implementations, the present inventions are not so limited, but rather cover various modifications, and equivalent arrangements.

What is claimed is:

1. A system for applying therapy to an eye, the system comprising:
   at least one energy conducting element configured to apply an initial amount of energy according to an initial pattern to an eye, the initial amount of energy according to the initial pattern causing a reshaping of an aspect of the eye, the at least one energy conducting element including an inner conductor and an outer conductor separated by a gap, a distal end of the outer conductor and the inner conductor defining the initial pattern;
   a measurement device operable to measure an amount of reshaping in response to an application of the initial amount of energy according to the initial pattern and provide a feedback indication of the measured amount of reshaping; and
   a controller operably coupled to the at least one energy conducting element and the measurement device, the controller being configured to:
      receive the feedback indication of the amount of reshaping from the measurement device and, in response, to the feedback indication of the amount of reshaping,
      determine a second amount of energy and a different pattern based on the feedback indication of the reshaping received from the measurement device, the at least one energy conducting element being configured to apply the second amount of energy according to the different pattern to the eye, and
      cause the at least one energy conducting element to apply the second amount of energy according to the different pattern to the eye, the second amount of energy according to the different pattern causing a different reshaping of the aspect of the eye.

2. The system according to claim 1, further comprising a plurality of replaceable end pieces, the distal end of the outer conductor and the inner conductor being defined by at least one of the plurality of replaceable end pieces.

3. The system according to claim 2, wherein each of the plurality of replaceable end pieces has a different shape.

4. The system according to claim 2, wherein each of the plurality of replaceable end pieces has different dimensions.

5. The system according to claim 2, wherein a first one of the plurality of replaceable end pieces is attached to the at least one energy conducting element to apply the initial amount of energy according to the initial pattern, and a second one of the plurality of replaceable end pieces is attached to the at least one energy conducting element to apply the second amount of energy according to the different pattern.

6. The system according to claim 1, wherein the at least one energy conducting element includes a first energy conducting element and a second energy conducting element, the distal end of the first energy conducting element defines the initial pattern, and the distal end of the second energy conducting element defines the different pattern.

7. The system according to claim 1, further comprising a sheet of dielectric material covering the distal end to provide a bottom surface of a substantially enclosed assembly that includes the at least one energy conducting element.

8. The system according to claim 7, further comprising:
   a coolant supply; and
   a coolant delivery system in communication with the coolant supply, the substantially enclosed assembly further including the coolant delivery system, the controller being further configured to cause the coolant delivery system to deliver a pulse of coolant to the dielectric material.

9. The system according to claim 1, wherein the measurement device includes keratometer.

10. The system according to claim 1, wherein the initial amount of energy according to the initial pattern is applied at a first location relative to the eye and the second amount of energy according to the different pattern is applied at a second location relative to the eye, the first location being different than the second location, the controller being configured to determine the second location based on the feedback indication of reshaping received from the measurement device.

11. The system according to claim 1, wherein the controller is further configured to compare the feedback indication of reshaping to a threshold amount of reshaping and determine whether to apply the second amount of energy according to the different pattern based on the comparison.

* * * * *